United States Patent [19]

Cantor et al.

[11] Patent Number: 5,616,466
[45] Date of Patent: Apr. 1, 1997

[54] RIBOZYME-MEDIATED INHIBITION OF BOVINE LEUKEMIA VIRUS

[76] Inventors: Glenn H. Cantor, NW. 517 Sunset; Guy H. Palmer, NW. 815 Fisk, both of Pullman, Wash. 99163

[21] Appl. No.: 520,226

[22] Filed: Aug. 28, 1995

Related U.S. Application Data

[63] Continuation of Ser. No. 148,208, Nov. 5, 1993, abandoned.

[51] Int. Cl.$^6$ .............................. C12Q 1/68; C12N 15/85; C07H 21/04; A61K 48/00
[52] U.S. Cl. ................. 435/6; 435/91.31; 435/172.3; 435/320.1; 536/23.1; 536/23.2; 536/24.5; 514/44
[58] Field of Search ................... 435/6, 91.31, 172.3, 435/320.1, 240.1, 240.2; 536/23.1, 24.5, 23.2; 514/44

[56] References Cited

U.S. PATENT DOCUMENTS 5,190,931  3/1993  Inouye ................................ 435/91.32

OTHER PUBLICATIONS

Katch et al. EMBO J. 8:497–503 (1989).
Willems et al. EMBO J. 6:3385–3389 (1987).
Derse J. Virol. 62:1115–1119 (1988).
Yu et al. PNAS 90:6340–6344 (1993).
Alexandersen et al. J. Virol. 67:39–52 (1993).
Sarver et al. Science 247: 1222–1225 (1990).
Johnston et al. Science 260:1286–1293 (1993).
Baringa Science 262: 1512–1514 (1993).
Tikhonenko et al. J. Cell. Biochem. Suppl. 15D, p. 37, abstract (1991).
"A Listing of Antisense Patents, 1971–1991," *Anti. Res. Dev.* 1:219–226 (1991).
Cantor, G. H. et al., "Antisense Oligonucleotide Inhibition of Bovine Leukemia Virus *tax* Expression in a Cell-Free System," *Anti. Res. Dev.* 2:147–152 (1992).
Cantor, G.H. et al., "Ribozyme Cleaves *rex/tax* mRNA and Inhibits Bovine Leukemia Virus Expression," *PNAS* (USA) 90:1–5 (1993).
Willems, L. et al., "In Vivo Infection of Sheep by Bovine Leukemia Virus Mutants," *J. Virol.* 67:4078–4085 (1993).

*Primary Examiner*—John L. LeGuyader
*Attorney, Agent, or Firm*—Harness, Dickey & Pierce, P.L.C.

[57] ABSTRACT

A ribozyme is provided which is capable of cleaving bovine leukemia virus (BLV) RNA both in a cell free system and intracellularly. The ribozyme of the present invention comprises the hammerhead motif flanked by antisense sequences complementary to BLV rex/tax RNA. Introduction of the ribozyme into BLV-infected cells results in inhibition of BLV protein expression, allowing for the control of BLV infection.

6 Claims, 3 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear     ( i i ) MOLECULE TYPE: RNA (genomic)

( i i i ) HYPOTHETICAL: NO

( i v ) ANTI-SENSE: YES

( x i ) SEQUENCE DESCRIPTION: SEQ ID NO:1:

CAUCAUUGCU GAUGAGUCCG UGAGGACGAA ACAAAACCA                                    39

( 2 ) INFORMATION FOR SEQ ID NO:2:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:2:

CATCATTGCT GATGAGTCCG TGAGGACGAA ACAAAACCA                                    39

RIBOZYME-MEDIATED INHIBITION OF BOVINE LEUKEMIA VIRUS

This is a continuation of U.S. patent application Ser. No. 08/148,208, filed Nov. 5, 1993, now abandoned.

Work on this invention was supported by the United States government under CSRS grant 91-37204-6818, awarded by the Department of Agriculture, and fellowship F32 Al08325, awarded by the National Institutes of Health.

FIELD OF THE INVENTION

The present invention relates generally to the inhibition of bovine leukemia virus (BLV) expression, and more particularly, to a method of controlling BLV infection by utilizing a ribozyme which cleaves viral RNA.

BACKGROUND OF THE INVENTION

Bovine leukemia virus (BLV) is a blood-borne disease primarily transmitted mechanically by vectors and fomites. Straub, O. C. in *Enzootic Bovine Leukosis and Bovine Leukemia virus*, eds. Burny, A. & Mammerickx, M. (Martinus Nijhoff, Boston, Mass.), pp. 229–249 (1987). Approximately 30% of infected cattle develop persistent lymphocytosis, a polyclonal expansion of B lymphocytes. Ferrer, J. F. et al., *J. Amer. Vet. Med. Assoc.* 175:705–708 (1979); Kettmann, R. et al., *Proc. Natl. Acad. Sci. USA* 79:2465–2469 (1982) and Miller, L. D. et al., *J. Nat. Cancer Inst.* 48:423–428 (1972). The development of persistent lymphocytosis, in which the absolute number of lymphocytes (International Committee on Bovine Leukosis *J. Nat. Cancer Inst.* 41:243–263 (1968)) and the percentage of infected lymphocytes are dramatically increased (Burny, A. et al., *Adv. Vet. Sci. Comp. Med.* 32:149–170 (1988) and Kettmann, R. et al., *Proc. Natl. Acad. Sci. USA* 77:2577–2581 (1980)), markedly enhances the probability of transmission. Mammerickx, M. et al., *Leuk. Res.* 11:353–358 (1987).

The critical importance of persistent lymphocytosis to transmission of this blood-borne disease was demonstrated by experiments showing that less than 0.3 µl of blood from cattle with persistent lymphocytosis was capable of transmitting BLV, while more than 1 ml of blood was necessary to transmit from infected cattle which did not have persistent lymphocytosis. Mammerickx, M. et al., *Leuk. Res.* 11:353–358 (1987). Moreover, vertical transmission from BLV-infected dams to their calves has been shown to be strongly correlated with persistent lymphocytosis. Agresti, A. et al., *Amer. J. Vet. Res.* 54:373–378 (1993).

In cattle, the ability to transmit BLV varies (Mammerickx, M. et al., *Leuk. Res.* 11:353–358(1987) and Weber, A. F. et al., *Amer. J. Vet. Res.* 44:1912–1915(1983)), and expression of antigen after in vitro culture has been shown to correlate with infectivity. Miller, L. D. et al., *Amer. J. Vet. Res.* 46:808–814 (1985). The level of BLV expression in the animal also may correlate with the probability of development of persistent lymphocytosis. Dropulic, B. et al., *J. Virol.* 66:1432–1441 (1992) and Cockerell, G. L. et al., *Leuk. Res.* 12:465–469 (1988). Moreover, persistent lymphocytosis is a strong risk factor for development of lymphoma. In 1–10% of the animals with persistent lymphocytosis, B cell clones undergo neoplastic transformation, leading to leukemia or lymphoma (Ferrer, J. F. et al., *J. Amer. Vet. Med. Assoc.* 175:705–708 (1979)), and cattle with persistent lymphocytosis are three times more likely to develop lymphoma than infected cattle without persistent lymphocytosis. Ferrer, J. F. et al., *J. Amer. Vet. Med. Assoc.* 175:705–708 (1979). BLV infection is thus a costly impediment to cattle production.

Currently, BLV is controlled by testing and slaughtering infected animals. Spread to newborn calves is reduced by raising them apart from their infected dams. However, in the United States, up to 66% of dairy herds are affected, and 13–48% of individual dairy cows carry the virus. Losses due to slaughter condemnation of cattle with tumors exceeds $42 million per year. In addition, the cattle industry suffers considerable losses due to inability to export cattle from BLV-positive herds to many foreign countries.

BLV, which causes the disease, is a retrovirus structurally similar to human T-cell leukemia viruses -I and -II (HTLV-I and -II). Burny, A. et al., *Adv. Vet. Sci. Comp. Med.* 32:149–170 (1988) and Miller, J. M. et al., *J. Dairy Sci.* 65:2194–2203 (1982). After initial infection, BLV expresses a doubly-spliced transcript which encodes the regulatory proteins, Tax and Rex. Sagata, N. et al., *FEBS Lett.* 192:37–42 (1985). Tax trans-activates the viral long terminal repeat (LTR) and cellular promoters, including those of c-fos and somatostatin, and may be involved in tumorigenesis. Katoh, I. et al., *EMBO J.* 8:497–503 (1989). Co-transfection experiments have demonstrated that Tax is necessary for viral expression in vitro. Willems, L. et al., *EMBO J.* 6:3385–3389 (1987); Rosen, C. A. et al., *EMBO J.* 5:2585–2589 (1986) and Derse, D., *J. Virol.* 62:1115–1119 (1988). Rex regulates the transition from early expression of the doubly-spliced transcript encoding regulatory proteins to the later expression of singly-spliced or unspliced transcripts which express the env gene or the gag and pol genes. Derse, D., *J. Virol.* 62:1115–1119 (1988). Recently, the 3' region of HTLV-I and BLV has been shown to encode RNA with alternative splice patterns which may express other regulatory proteins. Ciminale, V. et al., *J. Virol.* 66:1737–1 745 (1992); Koralnik, I. J. et al., *Proc. Natl. Acad. Sci. USA* 89:8813–8817 (1992) and Alexandersen, S. et al., *J. Virol.* 67:39–52 (1993).

Some success has been achieved in targeting RNA for cleavage and inactivation by means of antisense sequences. Haseloff, J. et al., *Nature* 334:585–591 (1988). Specific antisense sequences can be used to flank the hammerhead motif, first identified in plant RNA pathogens, which has been demonstrated to cleave the phosphodiester bond downstream of a GUC triplet. Also, ribozymes, particular forms of RNA, which can be targeted to attach to other RNAs and then enzymatically cleave them have been targeted to cleave a variety of sites of human immunodeficiency virus (HIV). Sarver, N. et al., *Science* 247:1222–1225 (1990); Heidenreich, O. et al., *J. Biol. Chem.* 267:1904–1909 (1992); Dropulic, B. et al., *J. Virol.* 66:1432–1441 (1992); Weerasinghe, M. et al., *J. Virol.* 65:5531–5534 (1991); Sioud, M. et al., *Proc. Natl. Acad. Sci. USA* 88:7303–7307 (1991) and Lo, K. M. S. et al., *Virology* 190:176–183 (1992).

It would thus be desirable to inhibit regulatory proteins in the BLV group of viruses. It would also be desirable to develop a ribozyme capable of cleaving rex/tax mRNA. It would further be desirable to develop expression plasmids containing such ribozyme DNA for transfection of BLV-infected cells and cleavage of BLV RNA. It would also be desirable to provide transgenic cattle which are resistant to BLV-induced persistent lymphocytosis and lymphoma.

SUMMARY OF THE INVENTION

The present invention comprises ribozymes which target bovine leukemia virus (BLV) RNA for cleavage. The ribozymes comprise a catalytic motif operatively-linked to antisense sequences complementary to BLV rex/tax RNA. The preferred catalytic motif is the hammerhead motif, however others such as the hairpin, are also considered as within the scope of the present invention. The present invention also comprises the DNA encoding the ribozymes of the present invention. The present invention further includes the DNA encoding the ribozymes which has been inserted into an expression vector, resulting in a ribozyme expression plasmid. In accordance with the principles of the invention, this vector may be used to transfect BLV-infected cells, resulting in cleavage of rex/tax mRNA. Transfection results in inhibition of the expression of the viral proteins p24 and Tax, as well as reverse transcriptase. The present invention is thus useful as a mechanism of viral RNA cleavage and prevention of viral protein expression. The present invention may therefore be used to decrease the severity of BLV-induced lymphocytosis and neoplasia in individual cattle, as well as to halt the spread of BLV within herds of cattle.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

BRIEF DESCRIPTION OF THE SEQUENCE LISTING

SEQ ID No. 1 corresponds to the ribonucleic acid (RNA) sequence of ribozyme 2.

SEQ ID No. 2, and more particularly, to the DNA sequence complementary to that encoding ribozyme 2 corresponds to the representative deoxyribonucleic acid (DNA) sequence of ribozyme 2.

DETAILED DESCRIPTION OF THE PREFERRED EMBODIMENTS

Ribozymes of the present invention comprise a catalytic motif operatively-linked to antisense sequences complementary to BLV rex/tax RNA, which target bovine leukemia virus (BLV) RNA for cleavage. The preferred catalytic motif of the present invention is the hammerhead motif, however others such as the hairpin may also be employed in the present invention. The DNA encoding the ribozymes of the present invention are also cloned into expression vectors, resulting in ribozyme expression plasmids. This vector may be used in accordance with the present invention to transfect BLV-infected cells to cleave rex/tax mRNA and inhibit expression of viral proteins, thus decreasing the severity of BLV-induced lymphocytosis and neoplasm in cattle.

The preferred ribozyme of the present invention is ribozyme 2. The ribonucleic acid (RNA) sequence of ribozyme 2 and the representative deoxyribonucleic acid (DNA) sequence for ribozyme 2 are set forth in SEQ ID No. 1 and SEQ ID No. 2, respectively. In a preferred embodiment, the DNA encoding ribozyme 2 may be cloned into an expression vector, resulting in the preferred ribozyme expression plasmid of the present invention, pRc/R2. The expression vectors and/or plasmids of the present invention may be used to transfect a population of cells, to cleave rex/tax mRNA and inhibit BLV protein expression in the cells. The transfection of the cell population may occur in vivo or in vitro. The present invention thus includes a method of treating and preventing BLV.

In contrast to previous studies of inhibition of HIV expression utilizing a ribozyme directed against gag, the studies and invention described herein involve the targeting of RNA encoding regulatory proteins, to amplify inhibitory effects. BLV transcribes at least three mRNAs, which, in addition to rex/tax mRNA, include the unspliced 9.2 kb message expressing the retroviral gag and pol gene products, and the singly spliced 5.1 kb message expressing the env gene products. Sagata, N. et al., *FEBS Lett.* 192:37–42 (1985) and Mamoun, R. Z. et al., *J. Virol.* 54:625–629 (1985). Recently, alternative splice patterns have been shown to result in additional transcripts which likely encode regulatory genes from the env-rex interregion. Alexandersen, S. et al., *J. Virol.* 67:39–52. (1993). All of these transcripts contain a long 3' untranslated region, which includes the sequences found in the rex/tax RNA, the target of ribozyme 2, which is shown herein to inhibit expression of BLV proteins. In a variety of mRNAs, the 3' untranslated region has been shown to be important for extending mRNA persistence and avoiding RNase digestion. Carter, B. Z. et al., *Lab. Invest.* 65:61 0–621 (1991). Thus, it is possible that ribozyme 2 not only cleaves rex/tax mRNA in its coding region, inhibiting its translation, but also accelerates the decay of other BLV transcripts.

The results described herein show that ribozyme 2 can cleave its target RNA both in a cell-free assay and within BLV-infected cells. In the RT-PCR intracellular cleavage assay, the ratio of short PCR product corresponding to cleaved RNA, to long product corresponding to uncleaved RNA, was markedly elevated, demonstrating intracellular cleavage. This ratio, 3.75, compares closely with previous reports of Dropulic, a ratio of 3.3 in a similar assay with a ribozyme directed against HIV. Dropulic, B. et al., *J. Virol.* 66:1432–1441 (1992). These figures should be regarded as minimal estimates of cleavage, because of the possibility of accelerated decay of the cleaved fragments. Carter, B. Z. et al., *Lab. Invest.* 65:61 0–621 (1991).

In contrast to the results with ribozyme 2, another similarly derived ribozyme, ribozyme 3, failed to cleave the target RNA. This finding emphasizes the importance of factors other than primary sequence in ribozyme action. For example, secondary structure such as a preexisting intramolecular RNA duplex may preclude access of a ribozyme to its target (Bertrand, E. et al., in *Gene Regulation: Biology of Antisense RNA and DNA,* eds. Erickson, R. P. & Izant, J. G. (Raven Press, New York), pp. 71–81 (1992) and Xing, Z. et al., *J. Virol.* 66:1361–1369 (1992)), or, if the ribozyme does hybridize with the target, alternative tertiary structures may form which are more favored than the hammerhead motif. Bertrand, E. et al., in *Gene Regulation: Biology of Antisense RNA and DNA,* eds. Erickson, R. P. & Izant, J. G. (Raven Press, New York), pp. 71–81 (1992).

Demonstration that this ribozyme or antisense (Cantor, G. H. et al., *Antisense Res. Dev.* 2:147–152 (1992); Borisenko, A; et al., *Virus Res.* 23:89–97 (1992) and Murovska, M. F. et al., *Vet. Microbiol.* 33:361–366 (1992)) inhibits viral expression in persistently infected cells provides a new avenue for BLV control. The present invention thus includes any ribozyme compressing a nucleic acid consisting of a catalytic motif operatively linked to an antisense sequence complementary to BLV RNA.

As referred to herein, the term "nucleic acid" is intended to mean natural and synthetic linear and sequential arrays of nucleotides and nucleosides, e.g. cDNA, mRNA and RNA and derivatives thereof. The term "encoding" is intended to mean that the subject nucleic acid may be transcribed and translated into either the desired polypeptide or the subject protein in a suitable vector, e.g. when the subject nucleic acid is linked to appropriate control sequences such as promoter and enhancer elements in a suitable vector (e.g. an expression vector) and when the vector is introduced into an appropriate system or cell. This term is meant to include any degeneracy of the genetic code which will result in the same translation product. By "substantially as shown" or "substantially similar" with respect to a nucleic acid is meant sufficiently similar in structure or sequence to encode the desired polypeptide or protein product, or with respect to a polypeptide, sufficiently similar in structure or sequence to serve its principal function.

Development of transgenic animals which are resistant to retroviral disease is also possible using the DNA encoding ribozymes capable of inhibiting BLV of the present invention. Recently, transgenic mice were developed which express antisense RNA targeted to the packaging sequences of Moloney murine leukemia virus. It has been shown that these transgenic mice do not develop leukemia on challenge. Han, L. et al., *Proc. Natl. Acad. Sci. USA* 88:4313–4317 (1991). Transgenic cattle which are resistant to BLV-induced persistent lymphocytosis and lymphoma can now be developed by transfecting fertilized bovine oocytes with expression plasmids containing DNA encoding BLV-inhibitory ribozymes. Offspring of these cattle could be commercially marketed in areas where BLV is prevalent. Moreover, genetic ability to resist disease could substantially augment the value of commercially available bull semen and cow embryos.

A method of screening for BLV by utilizing methods known to those skilled in the art, is also contemplated by the present invention. By contacting a sample of isolated RNA with the ribozyme of the present invention having antisense sequences complementary to BLV RNA and a marker, under conditions favorable for hybridization, (e.g. performing a Southern Blot with the "ribozyme probe" of the present invention), BLV RNA may be detected. In general, hybridization of the ribozyme of the present invention having complementary antisense sequences to BLV RNA requires at least 8 bases on the 5' end and 8 bases on the 3' end for specific binding. Hybridization under conditions "favorable for hybridization" generally refers to the conditions known to those skilled in the art and described herein.

The following Specific Examples further describe the present invention.

SPECIFIC EXAMPLE I

CELL-FREE CLEAVAGE OF TARGET RNA BY RIBOZYMES

Materials and Methods

Figure 1:
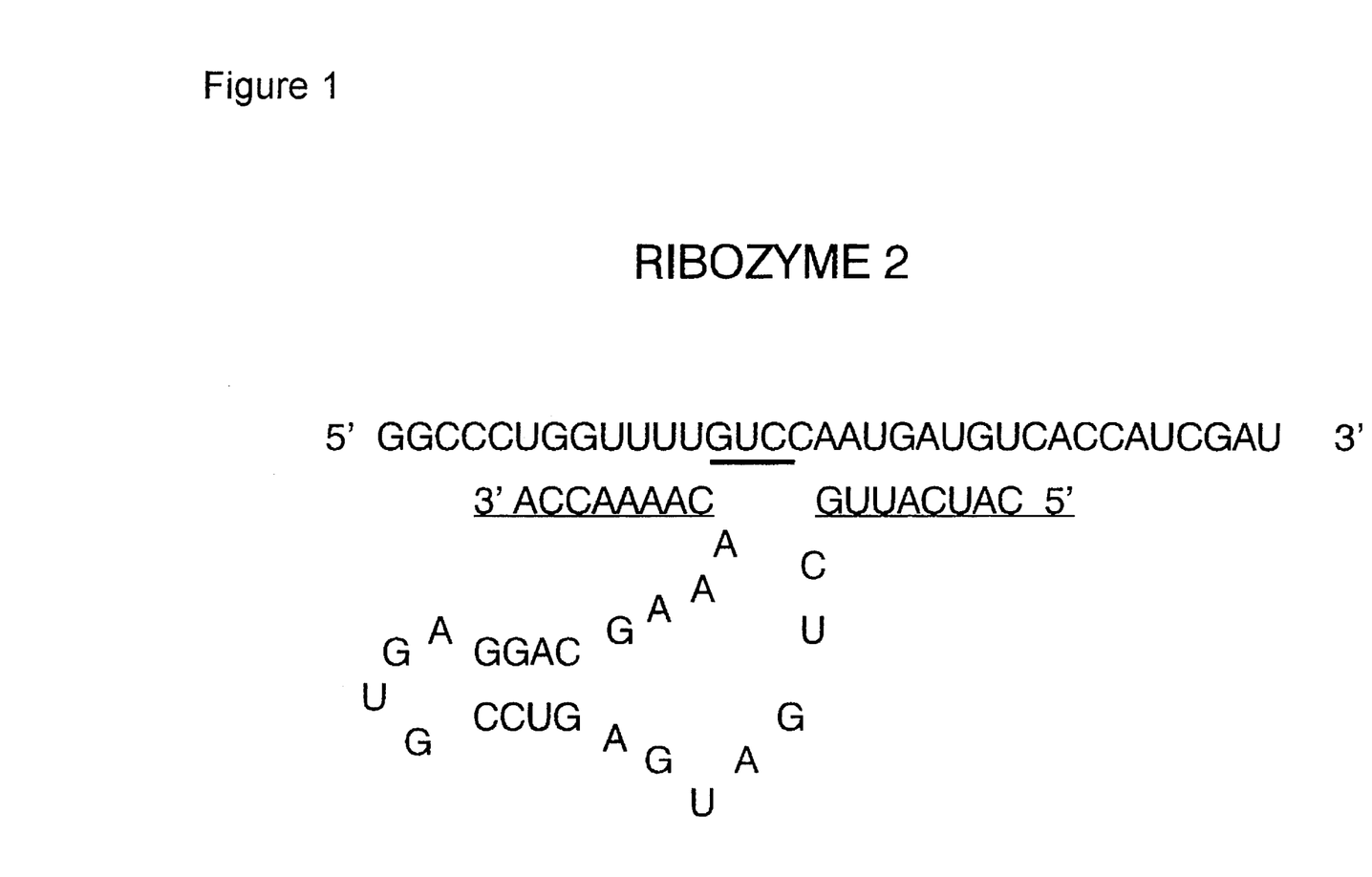
FIG. 1 is a diagram of ribozyme 2 hybridized to rex/tax mRNA.

Ribozymes. Ribozymes comprising the hammerhead motif (Sarver, N. et al., *Science* 247:1222–1225 (1990)) flanked by antisense sequences were targeted to cleave the rex/tax mRNA at nucleotide 7303 (ribozyme 2) (FIG. 1) or nucleotide 7680 (ribozyme 3) (nucleotides are designated by the numbering system of Sagata (Sagata, N. et al., *Proc. Natl. Acad. Sci. USA* 82:677–681 (1985))). The sequence of ribozyme 2 is 5' CAUCAUUGCUGAUGAGUCCGUGAG-GACGAAACAAAACCA (FIG. 1), and that of ribozyme 3 is 5' UUUCCGAGCUGAUGAGUCCGUGAGGAC-GAAACAGGAUGC. FIG. 1 shows the sequence of ribozyme 2 (bottom), hybridized to rex/tax mRNA (top). The underlined portions of ribozyme 2 are antisense sequences to target the rex/tax mRNA. Shown in FIG. 1 are bases 7289 through 7322 of the rex/tax mRNA; the ribozyme is designed to cleave downstream of the underlined GUC triplet (base 7303). Negative controls included a motif control, consisting of the hammerhead motif flanked by the random nonsense sequence 5' CAGAGUGU-CUGAUGAGUCCGUGAGGACGAAACAUUGGCA, and an antisense control, consisting of the antisense sequences of ribozyme 2, but in which the hammerhead motif was replaced by a single base, U (5' CAUCAUUG-CAUAAAACCA). RNA oligonucleotides were synthesized by National Biosciences, Inc. (Plymouth, Minn.).

Figure 2:
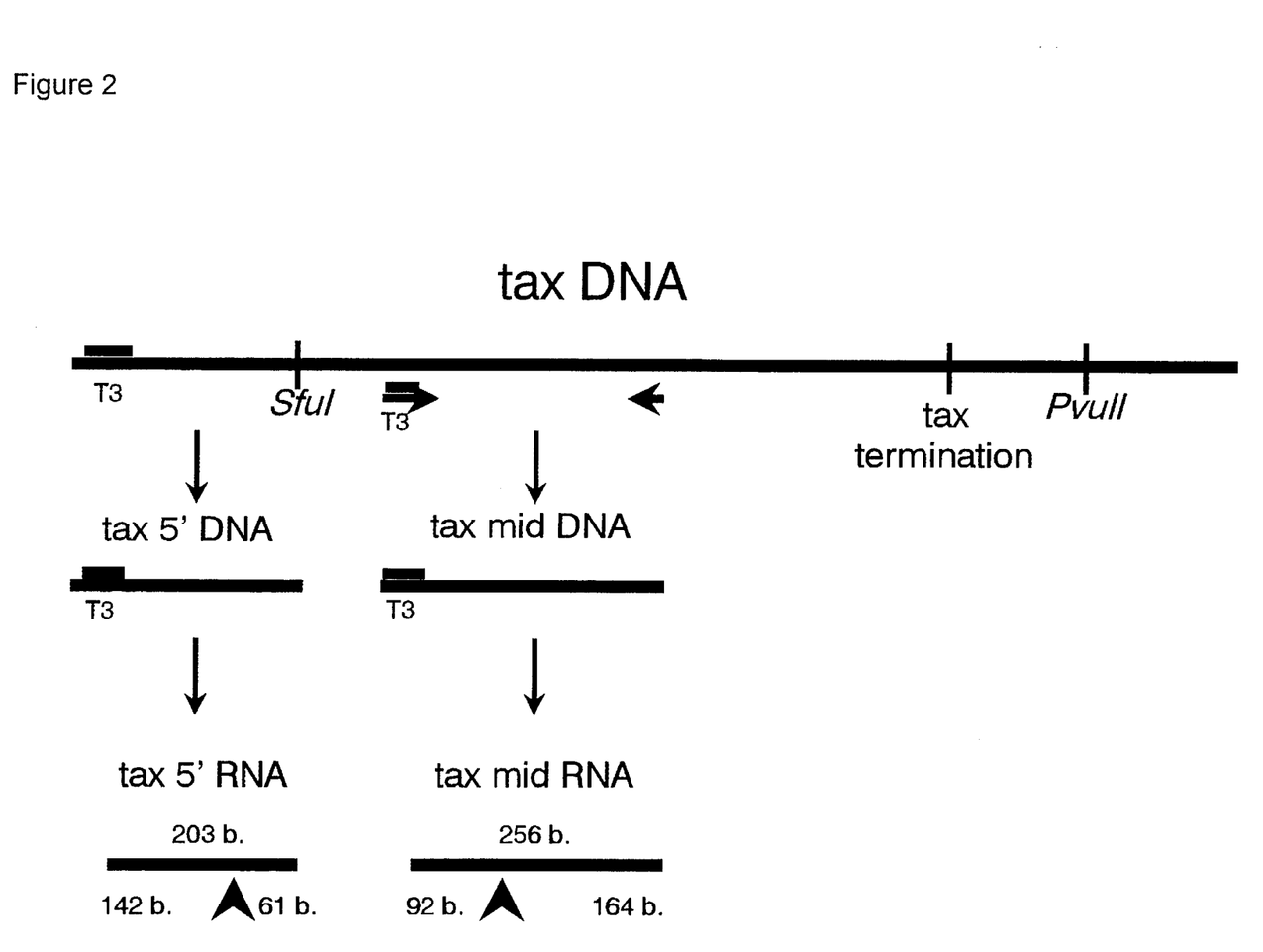
FIG. 2 is a schematic diagram of the derivation of tax 5' and mid-RNA substrates used in a cell-free cleavage assay.

Substrate RNA. FIG. 2 is a schematic representation of the derivation of the substrate RNAs used in the cleavage assay. As previously described, the plasmid pBT, shown on the top line of FIG. 2, contains a cDNA copy of tax but does not express the partially overlapping rex gene due to deletion of 44 bases at the 5' end. Cantor, G. H. et al., *Antisense Res. Dev.* 2:147–152 (1992). tax RNA was transcribed in vitro from PvuII-linearized pBT by using T3 RNA polymerase. Cantor, G. H. et al., *Antisense Res. Dev.* 2:147–152 (1992). Arrowheads designate predicted cleavage sites of ribozymes 2 and 3, and predicted sites of cleavage fragments are shown in FIG. 2. A 203 base portion of tax RNA, which included the target of ribozyme 2, was generated by linearizing pBT at the SfuI site (nucleotide 7364) and transcribing with T3 RNA polymerase in the presence of [$\alpha$-$^{32}$P]rCTP to yield radiolabelled RNA (FIG. 2). A 256 base RNA, including the target of ribozyme 3, was generated by polymerase chain reaction (PCR) amplification of pBT between nucleotides 7578 and 7834. The 5' primer also included the T3 RNA polymerase promoter sequence. The resulting PCR product was transcribed with T3 RNA polymerase (FIG. 2) in the presence of [$\alpha$-$^{32}$P]rCTP (Riboprobe Gemini System II, Promega).

Cell-free cleavage assay. Ribozyme and [$\alpha$-$^{32}$P]-labelled RNA were incubated in 50 mM Tris (pH 7.6 or 8.0) and MgCl$_2$. Initially, Mg$^{++}$ concentrations from 2 to 15 mM were used; 12.5 mM was found to be optimal. The RNA substrate concentration was 0.75 µM, and ribozyme concentrations varied from 0.375 µM to 15 µM. The ribozyme and RNA substrate in Tris were heated to 95° C. for two minutes, cooled on ice, and then MgCl$_2$ was added. Reactions were conducted at 37° C. or 50° C. for one hour, and the resulting RNA was subjected to electrophoresis in 8% polyacrylamide-7M urea gels. Gels were fixed in 10% methanol, 10% acetic acid, 1% glycerol, and autoradiographed with an intensifying screen. The relative amounts of each RNA species were quantitated by densitometry followed by correction for cytosine content.

Results

Figure 3:
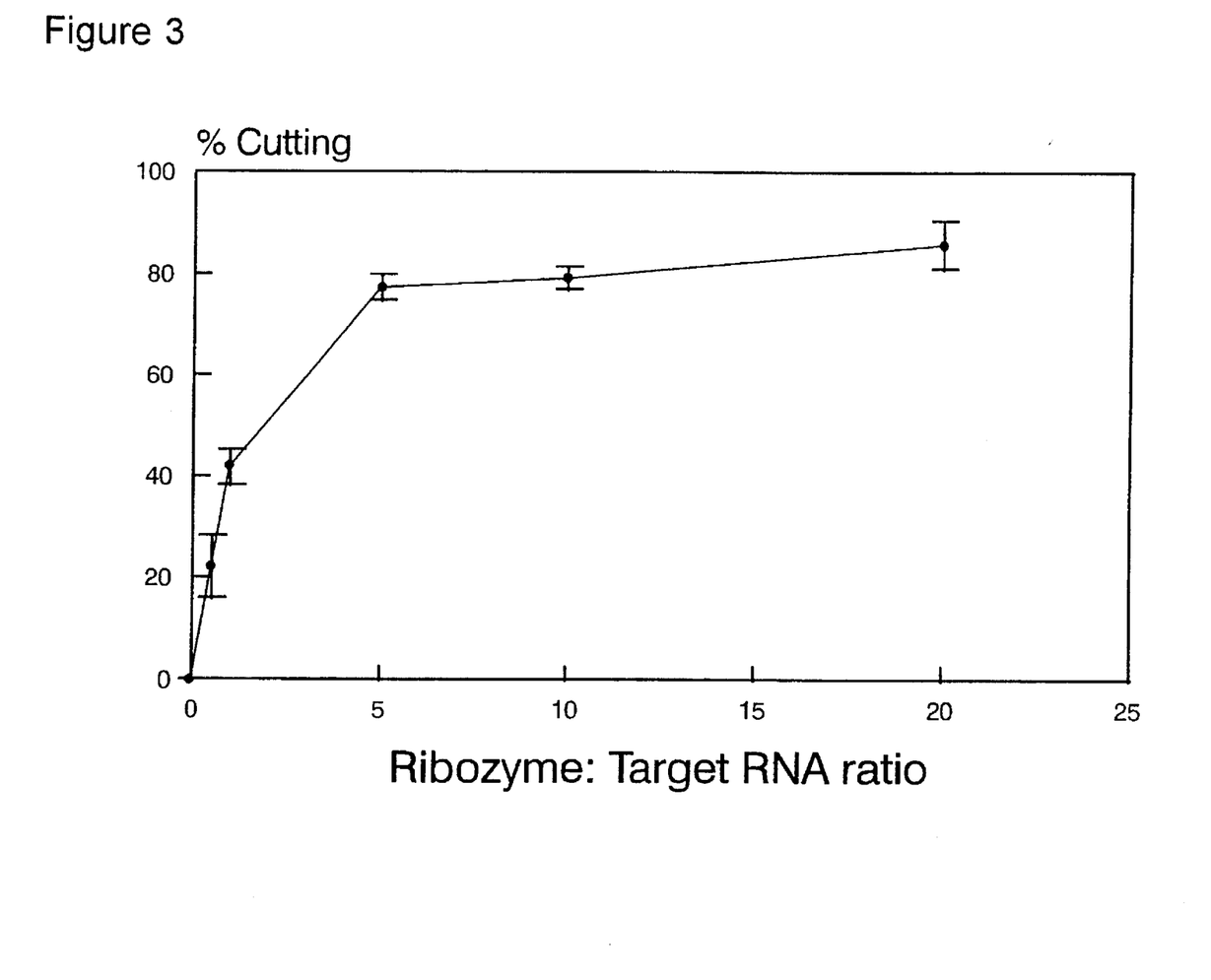
FIG. 3 is a dose response curve of cleavage of substrate RNA by ribozyme

Cell-free cleavage of target RNA. Incubation of ribozyme 2 with the 203 base substrate RNA from the 5' end of tax RNA resulted in the predicted 142 base and 61 base cleavage products. Cleavage products were not seen when substrate RNA was incubated with motif control RNA or with antisense RNA. FIG. 3 shows a dose-response curve of cleavage by ribozyme 2. As shown in FIG. 3, approximately 80% of the target RNA was cleaved when the ribozyme to target RNA ratio was more than 5:1. The 203 base substrate RNA (0.75 mM) was incubated with ribozyme 2 at concentrations ranging from 0.375 µM to 15 µM. The experiment was repeated three times; means and standard deviations are shown in the figure.

Ribozyme 3, directed at the middle of the tax RNA, failed to cleave its 256 base substrate RNA into the predicted 164 and 92 base products. No cleavage was observed, even at a variety of $Mg^{++}$ conditions (12.5 mM to 22.5 mM) and at molar ratios of up to 20:1, ribozyme to target RNA.

SPECIFIC EXAMPLE II

TRANSFECTION OF BLV-INFECTED CELLS WITH RIBOZYME EXPRESSION PLASMIDS

Materials and Methods

Cells. Bovine leukemia virus-infected bat lung cells (BLV-BLC) were used. Graves, D. C. et al., *Cancer Res.* 36:4152–4159 (1976). BLV infection was confirmed by identification of p24, gp51, and Tax by immunoblot, and by identification of intracellular p24 antigen by immunochemistry. Uninfected bat lung cells (Tb 1 Lu, CCL 88) were obtained from American Type Culture Collection (ATCC).

Ribozyme expression plasmids. Two eukaryotic expression plasmids were constructed: pRc/R2, which expresses ribozyme 2 RNA; and pRc/RMC, which expresses the motif control RNA, consisting of the hammerhead motif flanked by random nonsense sequence. The parental vector was pRc/RSV (Invitrogen), which has as a promoter the Rous Sarcoma Virus (RSV) long terminal repeat (LTR), a bovine growth hormone polyadenylation signal, and a Neogene under the control of the SV40 early promoter. Two strands of DNA oligonucleotides were synthesized to encode ribozyme flanked by a 5' HindIII site and a 3' XbaI site. Each strand was 5' phosphorylated using T4 polynucleotide kinase and the two strands annealed at 65° C. for 20 min, 45° C. for 1 hr, and 22° C. for 1 hr. After digesting concatamers with HindIII and XbaI, the ribozyme-encoding insert was ligated into the HindIII-XbaI sites of pRc/RSV and plasmid construction was confirmed by sequencing.

Transfection of bovine leukemia virus-infected bat lung cells. BLV-B LC were transfected with pRc/R2, pRc/RMC, or the parental plasmid, pRc/RSV, using calcium phosphate-DNA precipitate formed in N,N-bis(2-hydroxyethyl)-2-aminoethanesulfonic acid (BES) buffer, pH 6.95. Kingston, R. E. et al., in *Current Protocols in Molecular Biology*, eds. Ausubel, F. M., Brent, R., Kingston, R. E., Moore, D. D., Seidman, J. G., Smith, J. A. & Struhl, K. (J.Wiley & Sons, New York), pp. 9.1.1–9.1.9 (1989). Stably transfected, neo-expressing cell lines were selected in G418 for 25 days. Kingston, R. E. in *Current Protocols in Molecular Biology*, eds. Ausubel, F. M., Brent, R., Kingston, R. E., Moore, D. D., Seidman, J. G., Smith, J. A. & Struhl, K. (John Wiley & Sons, New York), pp. 9.5.1–9.5.6 (1989).

PCR analysis and Southern blots. Transfection of cell lines by ribozyme-encoding DNA sequences was verified by PCR amplification and Southern blotting. Genomic DNA was isolated using the TurboGen$^R$ kit (Invitrogen). Primer 1 was composed of RSV LTR bases 543–562 of the plasmid pRc/RSV (5' TTAAGTGCCTAGCTCGATAC) and primer 2 was from bases 750–730 (5' AGATGGCTGGCAACTAGAAG). These primers were chosen to amplify either a 208 base sequence, which includes the multiple cloning site, from the parental vector, pRc/RSV, or a 159 base sequence, which includes the ribozyme-encoding sequence, from pRc/R2. Negative controls included four reactions with no DNA. PCR was conducted with AmpliTaq® polymerase (Perkin Elmer) in 50 mM KCl, 10 mM Tris-HCl, pH 8.3, and 2.5 mM $MgCl_2$, using two amplifications, each consisting of 30 cycles of 95° C. for 90 sec, 60° C. for 90 sec, and 72° C. for 90 sec. PCR product was subjected to electrophoresis in a 1.5% agarose gel and transferred to positively-charged nylon membrane (Boehringer Mannheim). Membranes were probed with a synthetic DNA oligonucleotide from the 24 base ribozyme hammerhead motif (FIG. 1), which was 3' tailed with digoxigenin-11-dUTP/dATP (Genius system, Boehringer Mannheim). Hybridization conditions were 2 pmol/ml probe in 5x sodium chloride-sodium citrate (SSC), 1% blocking reagent, 0.1% N-laurylsarcosine, and 0.02% sodium dodecyl sulfate (SDS). Hybridization was carried out at 37° C. for 6 hours, followed by washes in 2x SSC containing 0.1% SDS at 22° C., and 0.5x SSC containing 0.1% SDS at 42° C. Chemiluminescent signal was detected by anti-digoxigenin antibody conjugated to alkaline phosphatase and Lumi-Phos 530 substrate, according to manufacturer's recommendations, followed by exposure to Kodak X-Omat AR film.

Results

PCR and Southern blot analysis of transfected cells. The presence of the hammerhead motif in BLV-infected cells transfected with the ribozyme-encoding plasmid pRc/R2 or with the motif-control plasmid pRc/RMC was demonstrated by PCR and Southern blotting. In genomic DNA isolated from each of these transfected cell lines, PCR amplified a 159 base pair fragment. On Southern blotting of these PCR products, the 159 bp fragment hybridized to a 24 base oligonucleotide derived from the hammerhead motif. The hybridizing band was not detected in untransfected cells and cells transferred with pRC/RSV (parental plasmid). PCR amplification was repeated on four separate days, using different preparations of genomic DNA from cells transfected with pRc/R2; all were positive for the 159 base fragment.

SPECIFIC EXAMPLE III

INTRACELLULAR CLEAVAGE OF rex/tax mRNA BY RIBOZYME 2

Materials and Methods

Intracellular cleavage assay (RT-PCR). Intracellular cleavage was evaluated by reverse transcriptase-PCR (RT-PCR). Total RNA was extracted by acid guanidinium thiocyanate-phenol-chloroform extraction (Puissant, C. et al., *Bio Techniques* 8:148–149 (1990)) from uninfected bat lung cells, BLV-infected bat lung cells (BLV-BLC), BLV-BLC transfected with the control plasmid pRc/RSV, and BLV-BLC transfected with the ribozyme plasmid pRc/R2. A negative control reaction contained no exogenous RNA. cDNA was synthesized with Moloney murine leukemia virus reverse transcriptase and random hexamer primers, according to the manufacturer's recommendations (Gene-Amp RNA PCR kit, Perkin Elmer Cetus). The rex/tax cDNA was PCR amplified using one upstream primer (5' AGGCGCTCTCCTGGCTACTG, from BLV nucleotides 4758–4776) (Sagata, N. et al., *Proc. Natl. Acad. Sci. USA* 82:677–681 (1985) and Jensen, W. A. et al., *J. Virol.* 65:2484–2490 (1991)) and two downstream primers, 5' GGCACCAGGCATCGATGGTG, from BLV nucleotides 7333–7314 (Sagata, N. et al., *Proc. Natl. Acad. Sci. USA* 82:677–681 (1985) and Jensen, W. A. et al., *J. Virol.* 65:2484–2490 (1991)) and 5' CCCCAACCAACAACACT-TGC, from BLV nucleotides 7265–7246 (17). These primers span the second splice junction of rex/tax mRNA, in order to specifically amplify the rex/tax transcript. Jensen, W. A. et al., *J. Virol.* 65:2484–2490 (1991). Primer 7265–7246 is upstream of the ribozyme 2 cleavage site (nucleotide 7303) and is chosen to amplify both cleaved and uncleaved rex/tax mRNA; primer 7333–7314 is downstream of the ribozyme cleavage site and should amplify only uncleaved rex/tax mRNA. PCR conditions were as described in Specific Example II, except that 2.0 mM $MgCl_2$ was used, and the melting time was 75 seconds. PCR products were subjected to electrophoresis in a 2.0% agarose gel and Southern blotted as above. Blots were probed with the oligonucleotide 5' GGCGTTTGCTGAAAGCCTTCAA, from BLV nucleotides 4798–4820 (Sagata, N. et al., *Proc. Natl. Acad. Sci. USA* 82:677–681 (1985)), as described in Specific Example 2, and autoradiographs were analyzed by densitometry. Cantor, G. H. et al., *Antisense Res. Dev.* 2:147–152 (1992).

Results

Intracellular cleavage. Ribozymes hybridize with target mRNA due to flanking antisense sequences, and then cleave. A ribozyme could inhibit gene expression by either an antisense effect or by cleavage of the target RNA. To verify that rex/tax cleavage occurred within the BLV-infected cells, RT-PCR was performed using one upstream primer and two downstream primers, one on either side of the ribozyme cleavage site. Uncleaved RNA is anticipated to produce both the short (133 bp) and the long (201 bp) PCR product; cleaved RNA is anticipated to produce only the short product. Templates for the reactions were total RNA from uninfected BLC, BLV-BLC, pRc/RSV (control plasmid)-transfected BLV-BLC, and pRc/R2 (ribozyme-encoding plasmid)-transfected BIV-BLC. When RNA from the pRc/R2 cell line was used in the assay, more short product than long was detected. When measured by densitometry, the ratio of short product:long product in the pRc/R2 cell line was 3.75. In contrast, ratios of BLV-infected cells without plasmid and with the control (pRc/RSV) plasmid were 1.0 and 0.82, respectively. Therefore, rex/tax mRNA was correctly cleaved in the pRc/R2 cell line by ribozyme 2.

SPECIFIC EXAMPLE IV

DETECTION OF BLV PROTEINS IN CELLS TRANSFECTED WITH RIBOZYME EXPRESSION PLASMIDS

Materials and Methods

Immunoblot analysis. Cells ($2.5 \times 10^6$) were lysed in 50 mM Tris, pH 7.4, 150 mM NaCl, 1% Triton X-100, 1% sodium desoxycholate, 0.1% SDS, and 1 mM phenylmethylsulfonyl fluoride, and were sonicated. Sagata, N. et al., *Proc. Natl. Acad. Sci. USA* 82:7879–7883 (1985). Lysates were subjected to electrophoresis in 7.5 to 17.5% polyacrylamide gradient gels, transferred to nitrocellulose, and reacted with Tax monoclonal antibody 5A5 (Chen, G. et al., *Virology* 173:343–347 (1989) and Willems, L. et al., *EMBO J.* 9:1577–1581 (1990)), followed by reaction with peroxidase-labelled goat anti-mouse IgG antibody (Kirkegaard Perry). Reactivity was detected using a chemiluminescent assay, according to manufacturer's recommendations ($ECL^R$, Amersham).

Immunochemistry to detect p24 expression. Monospecific polyclonal rabbit anti-BLV p24 antibody was used to detect intracellular p24 expression. A one kb p24-encoding SmaI fragment of BLV proviral clone pBLV913 was subcloned into pGEX2T and used to transform *E. coli*. The p24-glutathione transferase fusion protein was bound to a glutathione-sepharose column, and the p24 protein was cleaved from the glutathione transferase polypeptide using human thrombin. The purity of isolated p24 was confirmed in silver-stained SDS-PAGE gels. Rabbits were immunized with p24 using saponin as an adjuvant, and the specificity of the rabbit antibody for BLV p24 was confirmed by immunoblot analysis. Pre-immunization rabbit serum was used as a negative control.

Cells ($10^5$/well) were grown overnight in 96-well tissue culture plates, forming monolayers. The monolayers were fixed in 50% methanol, 50% acetone, 1.25% acetic acid, washed in PBS, and blocked with 0.7% swine gelatin and 0.1% Tween-20 in PBS, pH 7.2. The wells were incubated with rabbit anti-p24 antibody, diluted 1:1000 in blocking solution, for 37° C., 30 rain; washed in PBS; incubated with a 1:200 dilution of biotinylated anti-rabbit IgG antibody (Vector Labs) at 37° C., 30 min; washed; and incubated with avidin DH and biotinylated alkaline phosphatase H ($Vectastain^R$ ABCAP kit, Vector Labs). As a soluble substrate, 1.5 mg p-nitrophenyl phosphate/ml in 100 mM $NaHCO_3$, 10 mM $MgCl_2$, pH 9.5 was used. The substrate was reacted at room temperature for 12–15 min in the dark, and the reaction stopped with 0.2M EDTA, pH 7.2. Each reaction was performed in triplicate. Optical density was quantitated by absorbance at 405 nm and is expressed as the mean optical density of three wells reacted with p24 antiserum, minus the mean optical density of three wells reacted with pre-immunization serum. At least four different BLV-infected cell lines transfected with the control plasmid, pRc/RSV, were analyzed in each experiment. The optical densities of BLV-infected cell lines transfected with pRc/R2, the ribozyme-encoding plasmid, were compared to the mean and 99% confidence interval of the cell lines transfected with control pRc/RSV, and the percent inhibition was calculated. Uninfected bat lung ceils were included as a negative control.

Reverse transcriptase assay. Supernatant from $3\times10^6$ BLV-infected bat lung cells transfected with pRc/R2 (the ribozyme-encoding plasmid) or pRc/RSV (the control plasmid), or from uninfected bat lung cells was centrifuged at 1000 xg for 15 min, filtered (0.45 µm), and centrifuged at 100,000 xg for 30 min. The pellet was redissolved in reverse transcriptase buffer, consisting of 80 mM Tris, pH 8, 150 mM KCl, 0.02% Triton X-100, 5 mM dithiothreitol, 5 mM $MgCl_2$, 0.3 mM reduced glutathione, and 0.5 mM EGTA. Solubilized virus was incubated for 18 hrs at 37° C. with 20 µCi of $^3$H-dTTP and 2.5 µg of $poly(rA)/poly(dT)_{12-18}$ template. Labelled DNA product was precipitated with 10% trichloroacetic acid (TCA) and 20 mM sodium pyrophosphate, together with 25 µg tRNA, filtered through a glass fiber filter, and rinsed once with cold 10% TCA-20 mM sodium pyrophosphate and three times with 5% TCA. Scintillant was added and samples were counted.

Results

Tax expression. In immunoblot analysis using Tax monoclonal antibody 5A5, the expected 38 kD band was detected in lysate from BLV-infected cells transfected with the control plasmids pRc/RSV (cell line RSV30-3-4) or pRc/RMC (cell line RMC19-3), and in lysate from untransfected. BLV-infected cells. In contrast, the 38 kD Tax band was not detected in lysate from BLV-infected cells transfected with the ribozyme-expressing plasmid pRc/R2, nor in uninfected bat lung cells.

p24 expression. Intracellular expression of the BLV core protein p24 was assayed in cell monolayers by immunochemistry. In the experiment results of which are shown in Table 1, p24 expression in the pRc/R2-transfected cell line was inhibited 64.7%, as compared to the mean of four cell lines transfected with the control plasmid pRc/RSV. This experiment was repeated four times, with a mean percent inhibition of 60.8% (range 57.0 to 64.7% inhibition; standard error=1.7%). The mean optical density of the four control cell lines which were transfected with pRc/RSV (no ribozyme) was 0.237, and the 99% confidence interval was 0.125–0.350.

TABLE 1

Ribozyme Inhibition of p24 Expression

| Cell Type | Transfected Plasmid | Cell Line Designation | O.D.[a] | % Inhibition |
|---|---|---|---|---|
| BLV-infected BLC | pRc/RSV (no ribozyme) | RSV30-3-4 | 0.276 ± 0.009[b] | — |
| | | RSV30-1-1 | 0.244 ± .026 | — |
| | | RSV20-3-3 | 0.184 ± .009 | — |
| | | RSV20-1-2 | 0.245 ± .004 | — |
| | pRc/R2 (ribozyme) | R230-2-1 | 0.084 ± .012 | 64.7%[c] |
| Uninfected BLC | No plasmid | — | −0.004 ± .002 | 101.6% |

[a]Optical density is expressed as the mean optical density of three wells reacted with p24 antiserum, minus the mean optical density of three wells reacted with pre-immunization serum.
[b]The mean optical density of the four control cell lines which were transfected with pRc/RSV (no ribozyme) was 0.237, and the 99% confidence interval was 0.125–0.350.
[c]This experiment was repeated four times. The mean percent inhibition was 60.8% (range 57.0–64.7% inhibition; standard error = 1.7%).

In another experiment, p24 expression in pRc/RSV-transfected cell lines was compared with that in two pRc/RMC-transfected cell lines, which express RNA with the catalytic motif flanked by nonsense sequences. In these lines, p24 expression was similar to that in the pRc/RSV control lines.

Reverse transcriptase activity. Reverse transcriptase (RT) activity was measured in virus pelleted from tissue culture supernatant. The results of these experiments are shown in Table 2. Each assay was performed at least three times, and data were compared by analysis of variance on log-transformed data followed by a t-test on the corrected means. Different superscripts shown in Table 2 indicate significant differences ($p<0.05$). The corrected mean (cpm) reverse transcriptase activity was calculated by subtracting the background cpm, as determined from uninfected bat lung cells. The background in assay 1 was 181,783 cpm (s.d. 33,561) and the background in assay 2 was 18,039 (s.d. 7717). In supernatant from the cell line transfected with pRc/R2, RT activity was inhibited 86.1% and 98.6% as compared with a cell line (RSV 30-3-4) transfected with the control plasmid ($p<0.05$ in each assay) (Table 2).

TABLE 2

Ribozyme Inhibition of Reverse Transcriptase Activity

| Transfected Plasmid | Corrected Mean (cpm)* | Std. Dev. (cpm) | % Inhibition |
|---|---|---|---|
| Assay 1 | | | |
| pRc/RSV (no ribozyme) | 997,439[a] | 224,382 | |
| pRc/R2 (ribozyme) | 138,268[b] | 34,920 | 86.1% |
| Assay 2 | | | |
| pRc/RSV (no ribozyme) | 26,551[a] | 12,920 | |
| pRc/R2 (ribozyme) | 365[b] | 6,327 | 98.6% |

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims. All publications cited herein are incorporated by reference.

We claim:

1. A nucleic acid encoding a ribozyme wherein the nucleic acid has a sequence as set forth in SEQ ID No. 2.

2. A ribozyme expression vector, comprising the nucleic acid of claim 1 inserted into an eukaryotic expression vector.

3. A ribozyme expression plasmid comprising pRc/R2.

4. A method of inhibiting bovine leukemia virus protein expression in a cell population in vitro comprising the step of     transfecting the cell population with an expression vector comprising a nucleic acid having a sequence as set forth in SEQ ID No. 2.

5. The method of claim 4, wherein the expression vector is pRc/R2.

6. A method of inhibiting bovine leukemia virus mRNA expression comprising the step of     contacting the ribozyme encoded by SEQ. ID No. 2 to a bovine leukemia virus nucleic acid sequence under conditions favorable for hybridization.

* * * * *